United States Patent
Aubrun-Sonneville

(10) Patent No.: US 7,910,121 B2
(45) Date of Patent: Mar. 22, 2011

(54) SOLUBLE COSMETIC ARTICLE WITH A THERMAL EFFECT

(75) Inventor: Odile Aubrun-Sonneville, Antony (FR)

(73) Assignee: L'Oreal, Paris (FR)

( * ) Notice: Subject to any disclaimer, the term of this patent is extended or adjusted under 35 U.S.C. 154(b) by 931 days.

(21) Appl. No.: 11/567,867

(22) Filed: Dec. 7, 2006

(65) Prior Publication Data

US 2007/0128256 A1    Jun. 7, 2007

Related U.S. Application Data

(60) Provisional application No. 60/752,030, filed on Dec. 21, 2005.

(30) Foreign Application Priority Data

Dec. 7, 2005   (FR) ..................... 05 53750

(51) Int. Cl.
*A61K 8/02*    (2006.01)
*A61K 9/70*    (2006.01)
*B32B 27/06*   (2006.01)

(52) U.S. Cl. .................... 424/401; 424/443; 442/151

(58) Field of Classification Search .................. 442/151; 424/401, 443

See application file for complete search history.

(56) References Cited

U.S. PATENT DOCUMENTS

| 4,416,791 A | 11/1983 | Haq |
| 6,752,998 B2* | 6/2004 | Verdrel-Lahaxe et al. ... 424/401 |
| 2003/0073362 A1* | 4/2003 | Griesbach et al. ............ 442/151 |

FOREIGN PATENT DOCUMENTS

| EP | 0 750 905 | 1/1997 |
| EP | 1 172 088 | 1/2002 |
| GB | 2 302 651 | 1/1997 |
| WO | WO 2005/003423 | 1/2005 |

* cited by examiner

*Primary Examiner* — Taylor Victor Oh
(74) *Attorney, Agent, or Firm* — Oblon, Spivak, McClelland, Maier & Neustadt, L.L.P.

(57) ABSTRACT

An article having a support in the form of at least one sheet containing fibers that are water-soluble at a temperature of 0-30° C., the support having a density less than or equal to 0.1 g/cm$^3$, and a composition carried by the support, containing at least one compound with a thermal effect. The article can have a hot or cold effect depending on the nature of the compound(s) with thermal effect that is(are) present.

20 Claims, No Drawings

SOLUBLE COSMETIC ARTICLE WITH A THERMAL EFFECT

REFERENCE TO PRIOR APPLICATIONS

This application claims priority to U.S. provisional application 60/752,030 filed Dec. 21, 2005, and to French patent application 0553750 filed Dec. 7, 2005, both incorporated herein by reference.

FIELD OF THE INVENTION

The present invention relates to an article with a thermal effect, comprising at least one water-soluble support and at least one compound having an endothermic or exothermic reaction.

Additional advantages and other features of the present invention will be set forth in part in the description that follows and in part will become apparent to those having ordinary skill in the art upon examination of the following or may be learned from the practice of the present invention. The advantages of the present invention may be realized and obtained as particularly pointed out in the appended claims. As will be realized, the present invention is capable of other and different embodiments, and its several details are capable of modifications in various obvious respects, all without departing from the present invention. The description is to be regarded as illustrative in nature, and not as restrictive.

BACKGROUND OF THE INVENTION

Thermal effects are generally used in the field of skin care to supplement and/or amplify product efficacy.

Heat acting on the skin causes the pores to open, which improves the efficacy of a cosmetic composition applied on the skin. Thus, heating effects can be used notably in deep-cleansing products, such as exfoliating products containing abrasive particles, or in relaxing products. Heat will reinforce the sensation of deep cleansing or of relaxation. These heating effects can also be utilized in combination with actives or cosmetic agents which are rendered more active under the effect of heat.

Cooling effects are generally used in cleansing products when we wish to reinforce the sensation of freshness and the toning effect. They can also be used in care products, notably moisturizers for enhancing the sensation of hydration.

In general, these thermal effects are obtained by means of exothermic or endothermic compounds used as such or more generally used in anhydrous compositions containing exothermic or endothermic compounds. Most often, these anhydrous compositions contain a large amount of oils or of polyols and notably glycols.

Thus, document DE-A-10009252 describes cleansing gels containing at least 40% of polyols and water-soluble salts as particles. Document EP-A-1106164 describes solid cosmetic compositions, comprising a powder based on solid particles of expanded polymer and a binder containing oil and one or more agents that are capable of releasing heat, such as polyols and zeolite. Document EP-A-966956 describes pulverulent anhydrous compositions containing a powder based on solid particles of expanded polymer and a binder containing one or more agents capable of releasing heat, such as polyols and zeolite.

However, these compositions have poor cosmetic properties owing to the high levels of polyols which make the compositions sticky and heavy, or high levels of oils, which make them very greasy. Furthermore, very often it is useful to thicken these media for suspending the salts or zeolites required for producing the thermal effect. However, this operation is difficult owing to the poor swelling of the gelling polymers in these media.

Moreover, these compositions may impose formulation constraints, restricting the range of formulation to components that are soluble or dispersible in glycols or oils. These drawbacks are sometimes overcome by using two-compartment packaging articles enabling the heating composition to be separated from the other ingredients that are used in the composition, but are incompatible with the heating composition. Attempts are made to avoid using this complex packaging.

SUMMARY OF THE INVENTION

Therefore there is still a need for compositions with a thermal effect, without the drawbacks of those of the prior art, and notably displaying good cosmetic properties while providing the required, hot or cold, thermal effect.

The present invention meets this need. In fact, the inventor found, surprisingly, that it is possible to include compounds with a thermal effect in soluble supports, giving articles which, when moistened or dissolved in water at the moment of use, give compositions with a thermal effect, having good cosmetic properties.

The use of articles of this type can remove the formulation constraints, so that these articles can lead to a wide range of products, from gels to creams, for various applications, depending on the composition containing the compound with thermal effect, applied on the support. In addition, they are easy to manufacture.

DETAILED DESCRIPTION OF THE PREFERRED EMBODIMENTS

Thus, according to one of its aspects, the invention relates to an article, preferably a cosmetic or dermatologic article, comprising:

a support in the form of at least one sheet comprising fibres that are soluble in water at a temperature less than or equal to 30° C., said support having a density less than or equal to 0.1 g/cm$^3$, and a composition carried by the support, comprising at least one compound with a thermal effect.

The compound or compounds with thermal effect can be incorporated on the support as they are, but they can also be incorporated in a mixture with other components. The composition carried by the support may thus only comprise the compound or compounds with thermal effect which constitute the composition on their own, or it may contain the compound or compounds with thermal effect mixed with other components. This composition is generally preferably anhydrous, with "anhydrous" meaning here a composition that contains an amount of water less than or equal to 1%, and thus preferably in the range from 0 to 1% of the weight of the composition. This composition and the compound or compounds with thermal effect can advantageously, but not necessarily, be in the form of powder or of granules or in the form of a paste. This composition notably constitutes a cosmetic or dermatologic composition.

In the present application, the expression "carried by the support" means that the composition may be either placed on the support or introduced into the cavity formed by the support when the latter comprises at least two, e.g., sheets or layers, forming a cavity. Of course, both situations may occur in the same article depending on the extent of overlap of the at least two sheets or layers. "On the support" includes composition located in interstices of the support.

The expression "temperature less than or equal to 30° C." means a temperature that does not exceed 30° C. but is not less than 0° C., e.g., 0-30° C., for example ranging from more than 0° C. to 30° C., better still from 5° C. to 30° C., and even better still from 10° C. to 30° C., including 15, 20 and 25° C., and all ranges and subranges therebetween.

The terms "sheet" and "layer" are to be regarded as synonyms in the present application. The support of the present invention is preferably in the form of one or more sheets of fibres, which is different from the water-soluble thin films, which are not in the form of sheets of fibres. Compared with these water-soluble thin films, the supports based on water-soluble sheets of fibres according to the invention offer the advantage of permitting incompatible constituents to be incorporated, and to be easier to use as they do not require premixing or dissolution of the components, nor heating to evaporate the solvent, the procedure being quicker and less expensive. In addition, the supports according to the invention have the advantage of offering greater variety in the choice of shape and appearance of the article as the sheet of fibres can have variable thickness and density, giving access to a great variety of shapes and sizes without causing particular problems, whereas the thin film is difficult to dry if the thickness is too great, and it is fragile and difficult to manipulate if its size is too great.

According to a preferred embodiment of the invention, the article is in the form of a support having at least two sheets defining a cavity between them, with at least one of the sheets comprising fibres that are soluble in water at a temperature less than or equal to 30° C., said support having a density less than or equal to 0.1 g/cm$^3$, with the cavity containing a composition containing at least one compound with a thermal effect.

The sheets are preferably joined together at their periphery and thus form a cavity for introduction of the composition containing the compound with thermal effect.

The sheets can be formed entirely of water-soluble fibres or alternatively one of the sheets can be constituted entirely of soluble fibres and the other sheet can be constituted of insoluble fibres or of both water-soluble fibres and water-insoluble fibres, or the two sheets can be constituted of both soluble fibres and of insoluble fibres.

According to a preferred embodiment, at least one of the sheets is constituted exclusively of water-soluble fibres.

By moistening or dissolving the article according to the invention in water or in an aqueous composition, we obtain a composition for topical, notably cosmetic or dermatologic, application, giving a thermal effect.

The invention further relates, according to another of its aspects, to a composition for topical application obtained by dissolving an article as defined above in water, i.e. a composition obtained by dissolving, in water, a support in the form of at least one sheet comprising fibres that are water-soluble at a temperature less than or equal to 30° C., and having a density less than or equal to 0.1 g/cm$^3$, said support bearing a composition containing at least one compound with thermal effect. The composition obtained by dissolution of the article can be obtained from a support comprising one or more layers of fibres. The temperature of dissolution of the article in water is generally room temperature (20 to 30° C.) but can be higher than room temperature if required, depending on the use envisaged.

According to another of its aspects, the invention also relates to a method of cosmetic treatment of a keratinous material such as the skin, the hair, the mucosae and the integument, and notably for the cosmetic treatment of the skin, comprising:

the formation of a cosmetic composition by dissolving, in water, a support comprising at least one sheet comprising fibres that are soluble in water at a temperature less than or equal to 30° C., said support having a density less than or equal to 0.1 g/cm$^3$, and bearing at least one compound with a thermal effect, application of the composition thus formed on the keratinous material.

The cosmetic treatment comprises both care and make-up.

"Dissolution in water at a temperature less than or equal to 30° C." is to be understood as meaning dissolution in water at a temperature of up to 30° C. by means of manual agitation and/or friction of the support depending on circumstances, in a space of time typically less than 5 min, preferably less than 1 min, and preferably less than 30 seconds. The invention does not exclude using water at a temperature above 30° C. for dissolving the support.

As the article according to the invention is preferably intended for topical application, it comprises a physiologically acceptable medium. "Physiologically acceptable medium" means a medium that is compatible with keratinous materials such as the skin, lips, nails, scalp and/or the hair. This applies to the support, as well as to the composition carried by the support.

The article according to the invention preferably does not contain adhesive, but it may adhere to the skin when it is moistened.

The article is flexible. "Flexible" is to be understood as meaning an article that can be compressed or can be bent without breaking, and is capable of adapting to the relief of the human body. A flexible article made in the form of a fibrous sheet can in certain examples of application be folded over on itself at least once without breaking in two.

This article is generally preferably intended to be used once.

Moreover, the article is generally preferably dry to the touch prior to use.

After manufacture, the article can for example be packed loose in a box or in an individual packet. If applicable, the articles are packed in a string. The articles can also be folded on themselves and interposed, so that withdrawal of one article brings the next one into a configuration so that it can be grasped easily.

Thus, the invention further relates, according to another of its aspects, to a kit comprising:
  a packet,
  at least one article as defined above.

In the case of a coloured composition, the article can be packed in a packet containing, if applicable, a coloured sample representative of the colour of the composition obtained after dissolution of the article, for the purpose of informing the consumer prior to purchase.

The invention thus offers new possibilities for the packaging and formulation of cosmetic products with a thermal effect, and their uses, for example as hygiene or care products for the skin, the mucosae, the mouth or the hair or as make-up products.

In one example of application of the invention, the article formed by the support and the composition containing the compound with thermal effect, is brought into contact with water prior to use. The support is thus dissolved first, just before the article is applied on the human body. Depending on the amount of water added to the article to dissolve the support, the apparent viscosity of the composition obtained can easily be adjusted.

In another variant of application of the invention, the article formed by the support and the composition containing the compound with thermal effect is brought into contact with a region of the human body, for example the skin or the hair, before it dissolves completely, or even before it is wetted. This may make it possible for example, depending on the amount of water added, to modify the properties in relation to the desired result. The water can be poured or sprayed on the article while the latter is not in contact with the region of the body to be treated, or alternatively the region of the body can be wetted, or alternatively water can be sprayed or poured on the support while the article is in contact with the region to be treated.

Instead of using water, it is possible to use an aqueous composition to moisten the article, i.e. containing at least 50 wt. % of water relative to the total weight of the composition, and this composition can be in the form of lotion, milk, cream or a gel, notably a mousse-forming gel.

Support

The support is in the form of a sheet comprising water-soluble fibres, i.e. fibres that are soluble in water at a temperature less than or equal to 30° C., preferably soluble in water at a temperature less than or equal to 20° C., i.e. having a temperature of dissolution in water ranging from more than 0° C. to 30° C., preferably from more than 0° C. to 20° C., and for example from 50° C. to 30° C., and even better from 5 to 20° C.

The support can be substantially non-retractable once wetted.

Characteristically, the support has a density less than or equal to 0.1 g/cm$^3$, and more preferably in the range from 0.01 g/cm$^3$ to 0.1 g/cm$^3$, including 0.02, 0.04, 0.06 and 0.08 g/cm$^3$ and all values and subranges therebetween, which can provide a very aerated support, which accordingly dissolves more readily in water.

The support can have any shape, including any shape appropriate to the intended use, for example rectangular, round or oval shape, and it preferably has dimensions permitting it to be grasped between at least two fingers. Thus, the support can for example be of ovoid shape about 2 to 10 cm long and about 0.5 to 4 cm wide, or of disc shape with a diameter of about 2 to 10 cm, or in the form of a square with sides of about 5 to 15 cm, or in the form of a rectangle about 5 to 15 cm long, it being understood that it can have any other shape and size suitable for the required use.

The support can form, for example, a pad, a mask, a patch, a mobcap, a glove or a finger of a glove, a sheet for cutting out, a wipe, a disc, an oval or a rectangle. Moreover, the support can have a shape that depends on the region of the body to be treated.

The support can have a flattened form or a non-flattened form, for example having the appearance of a block formed from a globular mass of compacted water-soluble fibres, incorporating a composition containing a compound with thermal effect.

The fibres of the support are generally preferably interlaced to form the sheet of fibres. As stated above, "sheet comprising water-soluble fibres" means a sheet that can be constituted entirely of water-soluble fibres or a sheet that can comprise both water-soluble fibres and water-insoluble fibres, with a larger amount of soluble fibres than insoluble fibres. The sheet of fibres should preferably comprise at least 60 wt. % of soluble fibres, more preferably at least 70 wt. % and even more preferably at least 80 wt. % relative to the total weight of the fibres. It can thus comprise, for example, more than 95 wt. %, or even more than 99 wt. % and even 100 wt. % of water-soluble fibres relative to the total weight of the fibres of the support. Thus, the support can be constituted entirely of sheets of soluble fibres or it can be constituted of sheets comprising a mixture of soluble fibres and of insoluble fibres, the insoluble fibres being, as defined in the present invention, fibres that are not soluble in water at a temperature less than or equal to 30° C. The presence of insoluble fibres may make it possible to have a product with thermal effect which is at the same time a product for gentle exfoliation (dermabrasion), with the insoluble fibres constituting the exfoliating component.

Thus, the support can be formed from two sheets constituted of water-soluble fibres, or of one sheet constituted of water-soluble fibres and one sheet comprising both soluble fibres and insoluble fibres, or alternatively a sheet constituted of water-soluble fibres and a sheet constituted of water-insoluble fibres, or even two sheets comprising both soluble fibres and insoluble fibres. There can also be more than two sheets.

According to a preferred embodiment of the invention, the support does not have any water-insoluble fibres, but is composed solely of water-soluble fibres, so that it is completely soluble in water.

The soluble fibres can be of any soluble material that can be spun into fibres. Preferably, the water-soluble fibres are made from polyvinyl alcohol (PVA) by a method that endows them with the required solubility, and the PVA can have various degrees of polymerization.

PVA fibres that are soluble in water at a temperature less than or equal to 30° C. are marketed by the Japanese company KURARAY under the trade name KURALON K-II WN2. The method of manufacture of these fibres comprises preparation of a spinning solution by dissolving a water-soluble PVA-based polymer in a first organic solvent, spinning of the solution in a second organic solvent to obtain solidified threads and wet drawing of the threads from which the first solvent is removed and is then dried and undergoes a heat treatment. These fibres can be of roughly circular cross-section. These fibres have a tensile strength of at least 2.7 g/dtex (3 g/d). Application EP-A-0 636 716 describes such PVA-based water-soluble fibres and their method of manufacture.

The invention is not limited to the use of PVA, and it is also possible to use fibres made from other water-soluble materials provided that these materials dissolve in water of the required temperature, for example polysaccharide fibres marketed under the designation LYSORB by the company LYSAC TECHNOLOGIES, INC. or fibres based on polyholoside polymers such as glucomannan or starch.

The sheet of fibres can comprise, according to circumstances, a mixture of various fibres that are soluble in water at different temperatures (up to 30° C.).

The fibres can be composites, and they can comprise for example a core and a sheath that are dissimilar, for example formed from different grades of PVA.

When the sheet of fibres contains insoluble fibres, the latter can be of any material usually employed as insoluble fibres; they may for example be fibres of silk, cotton, wool, flax, cellulose extracted notably from wood, from vegetables or from algae, polyamide (Nylon®), polylactic acid, modified cellulose (rayon, viscose, acetate notably rayon acetate), poly-p-phenylene terephthalamide notably Kevlar®, of acrylic notably of methyl polymethacrylate, or of poly-2-hydroxyethyl methacrylate, of polyolefin and notably of polyethylene or of polypropylene, of glass, silica, aramid, of carbon notably in the form of graphite, of Teflon®, of insoluble collagen, of polyesters, of polyvinyl chloride or polyvinylidene chloride, polyvinyl alcohol, polyacrylonitrile, chitosan, polyurethane, polyethylene terephthalate, and fibres formed from a mixture of the compounds mentioned above, such as polyamide/polyester or viscose/polyester fibres. A general description of nonwovens is given in Riedel, Nonwoven Bonding Methods & Materials, Nonwoven World (1987), incorporated here by reference.

In a particular example of application of the invention, the sheet of the support is nonwoven, comprising water-soluble fibres, alone or mixed with insoluble fibres as stated above, with at most 40 wt. % of insoluble fibres relative to the total weight of the fibres constituting the sheet. Preferably, the nonwoven is constituted of water-soluble fibres, i.e. does not contain any insoluble fibres.

When the support only has one sheet of fibres, the composition containing the compound with thermal effect can be deposited on both faces of the support or on just one face, and the other face of the support can then be used for example for taking hold of the article.

When the support according to the present invention comprises two sheets, they can notably be two sheets of nonwoven, it being possible to use all the embodiments described hereunder, and the sheets may or may not contain insoluble fibres, and even one of the sheets can be constituted solely of insoluble fibres, as long as the other sheet contains soluble fibres.

According to a particular embodiment of the invention, each of the sheets is a nonwoven constituted of fibres that are soluble at a temperature less than or equal to 30° C., i.e. the sheets only comprise water-soluble fibres.

According to another embodiment, one of the sheets is completely soluble in water and is a nonwoven constituted of fibres that are soluble at a temperature less than or equal to 30° C., and the other sheet is insoluble and is a nonwoven constituted of insoluble fibres.

According to yet another embodiment, the support comprises two sheets containing fibres that are soluble or partially soluble with at most 40% of insoluble fibres, and in addition a sheet constituted of insoluble fibres, constituting an insoluble substrate. Thus, the support can comprise at least one layer of a water-insoluble substrate, i.e. only comprising insoluble fibres. In a particular example of this embodiment, the support comprises a soluble sheet of a nonwoven constituted of fibres that are soluble in water at a temperature less than or equal to 30° C., and an insoluble sheet of a nonwoven constituted of fibres that are insoluble in water.

A multilayer structure with at least one layer formed from a water-insoluble substrate can be used for example for making an article comprising a support in the shape of a finger of a glove. The layer formed from water-soluble fibres is located on the outside of the article, and is intended to dissolve during use, after being wetted or on coming into contact with a wetted region of the body.

For the manufacture of sheets in nonwovens, whether soluble or insoluble, all the suitable techniques for making a nonwoven material from fibres can be used. For example, the fibres can be formed by extrusion and deposited on a conveyor to form a sheet of fibres which is then consolidated by a conventional fibre bonding technique, for example needling, hot bonding, calendering or bonding by jets of hot air (called air through bonding), a technique in which the sheet passes through a tunnel into which hot air is blown. This last-mentioned technique is used advantageously when the sheet is constituted of two-component fibres, for example fibres comprising at least two grades of polyvinyl alcohol (PVA), having different melting points or softening points, these fibres being for example co-extruded in such a way that the fibre is constituted of at least one first grade located in the core of the fibre and at least one second grade located at the periphery of the fibre, in the form of a sheath. Bonding of the fibres may be easier when the sheath has a lower melting point than the core.

The sheet of fibres can also be formed by carding of fibres cut to a length of 10-50 mm, then deposition of the fibres on a conveyor where the sheet can then be consolidated by a bonding technique as described above.

When the support comprises several layers, whether or not the latter are all made with water-soluble fibres, the various layers can be joined together in a variety of ways, for example by welding, gluing or stitching, and these layers can constitute, according to circumstances, one or more cavities containing one or more cosmetic or dermatologic compositions or several components of one and the same cosmetic composition for mixing at the time of use. In the case of assembly by stitching, a thread that is itself water-soluble can be used, if required.

When the support comprises several nonwoven sheets, these can be joined together notably by heat-sealing at their periphery so as to constitute a pad, an internal cavity of which can hold a composition containing the compound with thermal effect.

According to another aspect of the invention, the support is not provided with adhesive, notably pressure-sensitive adhesive.

The composition containing at least one compound with thermal effect represents between 10 and 1000 wt. % relative to the weight of the support, and preferably between 10 and 500 wt. % relative to the weight of the support, where "weight of the support" means in this case the weight of the support alone, without the weight of the composition containing the compound with thermal effect. If the composition only contains the compound with thermal effect, it is the latter that can represent between 10 and 1000 wt. % relative to the weight of the support, and preferably between 10 and 500 wt. % relative to the weight of the support.

Compounds with Thermal Effect

In the present application, "compounds with thermal effect" means compounds that cause a temperature change when they are brought into contact with water, which can take place as a result of addition of water at the moment of application on keratinous material such as the skin, or simply by application on keratinous material, with the water necessary for the exothermic or endothermic reaction being supplied directly by the keratinous material itself, whether or not wetted beforehand, or being supplied after application on the keratinous material. These compounds are notably endothermic or exothermic compounds.

The article of the invention contains one or more compounds that are able to cause a temperature change, i.e. release heat or cold, on coming into contact with water. The amount of compound(s) with thermal effect preferably is such that the user effectively perceives a hot effect or a cold effect during use of the article. The compound or compounds with thermal effect can represent 100% of the composition carried by the support. They can be present in an amount ranging for example from 10 to 100% of the total weight of the composition carried by the support, and preferably from 20 to 100 wt. % relative to the total weight of the composition carried by the support. In the present application, "wt. % relative to the total weight of the composition" means the percentage by weight relative to the total weight of the composition carried by the support (and not relative to the weight of the article comprising support and composition).

As compounds giving hot effects—exothermic compounds—included are the zeolites (activated or inactivated), exothermic inorganic salts, polyols having at least 2 hydroxyl groups and at least 3 carbon atoms, ethers of vanillyl alcohol, gingerol; capsaicin and its derivatives; eugenol; cinnamon oil; benzyl alcohol, redox systems, and mixtures thereof.

The following examples of zeolites (aluminosilicates) may especially be mentioned: zeolites A, zeolites X such as those marketed by the companies Fluka and Union Carbide, zeolites MAP as described in document EP-A-384070, activated zeolites A as described in document EP-A-187912. The cations present in the zeolites used notably comprise Na, K, Ca, Zn, Mg, Li, Cu and combinations thereof.

The following may be mentioned more particularly as exothermic inorganic salts: calcium chloride, magnesium chloride, and mixtures containing them.

The following may notably be mentioned as polyols having at least 2 hydroxyl groups and at least 3 carbon atoms: glycerol, diglycerol, propylene glycol, butylene glycol, hexylene glycol, polyethylene glycol and the polyethylene glycols of molecular weight below 600 such as PEG-8, sugars such as sorbitol, and mixtures thereof.

The following may be mentioned as examples of ethers of vanillyl alcohol: n-butyl ether of vanillyl alcohol, n-propyl ether of vanillyl alcohol, isopropyl ether of vanillyl alcohol, isobutyl ether of vanillyl alcohol, isoamyl ether of vanillyl alcohol, n-hexyl ether of vanillyl alcohol, methyl ether of vanillyl alcohol, ethyl ether of vanillyl alcohol.

The redox systems can notably be based on a combination of iron powder and a catalyst with high specific surface, such as alumina, aluminosilicate, silica or charcoal, the weight ratio of iron powder to catalyst ranging for example from 1000:1 to 1:1000. Such a system is described for example in document WO-A-01/12133.

The following may be especially mentioned as compounds giving cold effects (endothermic compounds): endothermic inorganic salts such as potassium chloride; mint and its derivatives, or nitrogen-containing compounds such as urea.

The following may be especially mentioned as examples of derivatives of mint: menthol, peppermint oil, wintergreen, menthone, menthyl lactate, spearmint, mint oil; derivatives of menthane such as N-substituted menthane carboxamides, 3-(1-menthoxy)-propane-1,2-diol, p-menthane-3,8-diol, menthyl succinate and its alkaline-earth salts, and mixtures thereof.

According to a preferred embodiment of the invention, the compounds with thermal effect are preferably in the form of powder or paste, and most preferably in the form of powder. It is also possible to use liquid compounds which can for example be absorbed on powders or encapsulated before being placed on the support or mixed with other compounds in the composition placed on the support.

As mentioned above, the compounds with thermal effect used according to the invention can be placed on the support as they are or they can be incorporated in a composition that is placed on the support.

Compositions

The compositions containing the compound or compounds with thermal effect are preferably anhydrous compositions. They are preferably in the form of powder or paste, and more preferably in the form of powder. They are compositions that are suitable for topical application, and notably cosmetic or dermatologic compositions.

Thus, the compositions that can be used in the invention include:

lyophilized or atomized emulsions, such as those described in document FR-A-2,727,312 or those based on modified starch described in document EP-A-0 938 892. These emulsions are obtained by lyophilization or atomization of an O/W emulsion containing a pulverulent phase, foaming compositions in the form of powders, containing pulverulent surfactants, such as those based on starch, described in document EP-A-0 925 777, oil-free pulverulent compositions, containing mainly gelling agents (polymers, clays) and/or surfactants, compositions obtained by simple mixing of the constituents, the latter preferably being in the form of powders.

The composition may contain just the compound with thermal effect, which then represents 100% of the weight of the composition.

Depending on the constituents of the compositions used, the article is transformed to, e.g., milk, cream, mousse, gel, or lotion after moistening.

The composition can if necessary contain a certain amount of water at the moment of its impregnation on the support. However, to prevent its premature dissolution, the water introduced on the support during its impregnation should preferably be removed, for example heating. However, the composition can contain a certain amount of water which is generally bound water and which may originate notably from hygroscopic raw materials that contain water, such as starches. The final amount of water in the composition present on the article is at most 10 wt. % and preferably at most 5 wt. % relative to the total weight of the composition.

When the composition must be deposited on the support by the user, the composition and the support can be supplied together, in the form of a kit, for example. The composition is for example supplied in a sufficient amount for distributing a plurality of doses thereof on a set of supports that are to be used successively.

Other Ingredients

The other ingredients of the composition containing the compound with thermal effect depend on the final use of the article. The following examples of other ingredients may be mentioned in particular: mousse-forming surfactants, polymers, lipophilic compounds, exfoliating agents, as well as the active agents and additives usually employed in the particular fields. If necessary, the additives can be encapsulated or adsorbed on powders.

According to a particular embodiment of the invention, the composition carried by the support additionally contains at least one component selected from the mousse-forming surfactants, polymers, lipophilic compounds, exfoliating agents, actives, and mixtures thereof.

Mousse-Forming Surfactants

When the article according to the invention is to provide a mousse-forming or cleansing composition, the composition containing the compound with thermal effect contains in addition at least one mousse-forming surfactant, preferably in pulverulent form (powder). The mousse-forming surfactants that can be used are all those usually employed in the cosmetic field, and these surfactants can be anionic, non-ionic, cationic, amphoteric or zwitterionic.

The amount of mousse-forming surfactant(s) can range for example from 2 to 80 wt. %, preferably from 10 to 70 wt. % relative to the total weight of the composition.

The following may be particularly mentioned as examples of anionic mousse-forming surfactants: the salts of fatty acids which constitute soaps and are derived from a fatty acid having an alkyl chain with 6 to 22 carbon atoms, preferably 8 to 18 carbon atoms, and notably salts obtained by neutralizing a fatty acid with an organic or inorganic base such as potassium hydroxide, sodium hydroxide, triethanolamine, N-methylglucamine, lysine and arginine. As salts of fatty acids (soaps), we may notably mention the alkaline salts and for example the potassium or sodium salts of lauric, myristic, palmitic and stearic acids (potassium or sodium laurate, myristate, palmitate and stearate).

The following may also be particularly mentioned as anionic surfactants: alkyl sulphates and alkyl ether sulphates; sulphonates; alkaline salts of N-acylamino acids such as the sarcosinates, alaninates, glutamates, aspartates, glycinates; and mixtures thereof.

The following may be particularly mentioned as examples of non-ionic surfactants: sugar esters, sugar ethers such as alkyl polyglucosides (APG), condensates of alkylene oxides and alkyl phenols, ethers of fatty acid and polyols, and mixtures thereof.

Amphoteric or zwitterionic surfactants that may be particularly mentioned are the betaines and their derivatives, the sultaines and their derivatives, the derivatives of imidazolinium, and mixtures thereof.

The preferred surfactants are those in powder form, for example sodium lauryl sulphate such as the product marketed under the designation Empicol LZ D by the company Allbright & Wilson or under the designation Tensopol USP97 by the company Tensachem; cocamidopropylbetaine such as the product marketed under the designation Tegobetain CK D by the company Degussa; sodium lauroyl glutamate such as the product marketed under the designation Amisoft LS 11 by the company Ajinomoto; monosodium myristoyl glutamate such as the product marketed under the designation Acylglutamate MS 11 by the company Ajinomoto; the mixture of sodium laureth sulphate and silica, marketed under the designation Texapon KE 2713 by the company Cognis; disodium cocamido MEA-sulphosuccinate such as the product marketed under the designation Mackanate CM 100 by the company MacIntyre; sodium methyl cocoyl taurate, such as the product marketed under the designation Tauranol WSP by the company Finetex; sodium decyl d-galactoside uronate such as the product marketed under the designation Sodium decyl d-galactoside uronate by the company Ard-Soliance; lauroyl methyl beta-alanine (acid form) marketed under the designation LMA-H by the company Mitsui Toatsu; n-lauroyl-n-hydroxyethyl-beta-alanine marketed under the designation LHEA by the company Mitsui Toatsu; sodium cocoyl glycinate marketed under the designation Amilite GCS-11(F) by the company Ajinomoto; sodium cocoyl isethionate such as the product marketed under the designation Jordapon CI P by the company BASF; sodium lauryl sulphoacetate, such as the product marketed under the designation Lathanol LAL powder by the company Stepan; potassium myristate such as the product marketed under the designation Potassium myristate (DUB MK) by the company Stéarineries Dubois; potassium laurate such as the product marketed under the designation Potassium laurate (DUB LK) by the company Stéarineries Dubois, and sucrose laurate such as the product marketed under the designation Grilloten LSE 87 by the company Degussa.

According to a preferred embodiment of the invention, when the article according to the invention is to provide a mousse-forming or cleansing composition, the composition containing the compound with thermal effect contains at least one anionic mousse-forming surfactant.

Polymers

The composition carried by the support can also contain one or more polymers, notably water-soluble polymers. The following may be particularly mentioned as examples of water-soluble polymers that can be used in the invention: guar, xanthan, carrageenan, cellulose and sclerotium gums, derivatives of these gums, hydroxyalkyl celluloses, carboxymethylcellulose, polyacrylamides and acrylamide copolymers and notably the homopolymers and copolymers of 2-acrylamido-2-methylpropanesulphonic acid such as those marketed under the designations Hostacerin AMPS and Aristoflex by the company Clariant, gelatin, agar-agar, carboxyvinyl polymers such as the products marketed under the designations Carbopol by the company Noveon (INCI name: carbomer), modified carboxyvinyl polymers and notably acrylate/$C_{10}$-$C_{30}$-alkylacrylate copolymers such as the products marketed under the designations Pemulen TR1 or TR2 or CARBOPOL 1382 by the company Noveon (INCI name: Acrylates/C10-30 Alkyl acrylate Crosspolymer), montmorillonite and the silicate of magnesium and aluminium.

When they are present, the amount of polymer(s) in the composition of the invention can range for example from 0.1 to 80% and preferably from 0.5 to 70% of the total weight of the composition carried by the support.

Lipophilic Compounds

The composition according to the invention can also contain one or more lipophilic compounds, fats and notably oils, or oily active. The amount of lipophilic compound can range for example from 1 to 80 wt. % relative to the total weight of the composition carried by the support.

It is possible to use any kind of oil and fat familiar to a person skilled in the art, such as oils of vegetable origin (for example jojoba, avocado, sesame, sunflower, maize, soya, safflower, grapeseed oils), mineral oils (for example vaseline, isoparaffins, optionally hydrogenated), synthetic oils (for example isopropyl myristate, cetearyl octanoate, polyisobutylene, ethyl-hexyl palmitate or myristate, alkyl benzoates), volatile or non-volatile silicone oils, and fluorinated or fluorosiliconized oils, as well as mixtures of these oils.

The following may be particularly mentioned as other fats: fatty alcohols such as stearyl alcohol, cetyl alcohol and their mixture (cetearyl alcohol), fatty acids, gums, for example silicone gums such as the PDMS mixture with hydroxylated alpha-omega groups/PDMS 5 cSt (12/88) sold under the designation DC 1503 by the company Dow Corning, and the lipophilic gelling agents such as bentone.

Exfoliating Agents

The composition can also contain exfoliating agents, notably to constitute a composition for exfoliation or dermabrasion for the face or the body. The following examples of exfoliating agents may be particularly mentioned: exfoliating particles of mineral, vegetable or organic origin. Thus, for example, it is possible to use polyethylene beads or powder, nylon powder, polyvinyl chloride powder, pumice powder, ground apricot stones or nut shells, sawdust, glass beads, alumina, and mixtures thereof. Furthermore, as mentioned above, the exfoliating agent can be constituted of insoluble fibres included in the sheet of fibres of the support.

The exfoliating particles can be present in an amount ranging for example from 0.5 to 40 wt. %, preferably from 1 to 20 wt. % and even better from 1 to 10 wt. % relative to the total weight of the composition. When the composition contains exfoliating particles, the article obtained can be used notably for exfoliation of the skin of the face or of the body.

Actives

The actives can be selected notably from the keratolytic agents, moisturizers, soothing agents and antimicrobials. If necessary, the actives can be encapsulated or can be adsorbed on powders.

We may particularly mention, as moisturizers, the polyols such as glycerol; compounds acting on the barrier function, in order to maintain the hydration of the stratum corneum, or occlusive compounds, in particular the ceramides, sphingoidbased compounds, lecithins, glycosphingolipids, phospholipids, cholesterol and its derivatives, phytosterols (stigmasterol, β-sitosterol, campesterol), essential fatty acids, 1,2-diacylglycerol, 4-chromanone, the pentacyclic triterpenes such as ursolic acid, vaseline and lanolin; compounds that directly increase the water content of the stratum corneum, such as threalose and its derivatives, hyaluronic acid and its derivatives, glycerol, pentanediol, sodium pidolate, serine, xylitol, sodium lactate, glycerol polyacrylate, ectoin and its derivatives, chitosan, oligosaccharides and polysaccharides, cyclic carbonates, N-lauroyl pyrrolidone carboxylic acid, and N-α-benzoyl-L-arginine; and mixtures thereof.

The following may be mentioned as keratolytic agents: the β-hydroxyacids, in particular salicylic acid and its derivatives (including n-octanoyl-5-salicylic acid); the α-hydroxyacids, such as glycolic, citric, lactic, tartaric, malic or mandelic acids, and mixtures thereof.

The following may be particularly mentioned as examples of soothing agents that can be used in the composition according to the invention: pentacyclic triterpenes and plant extracts (e.g. *Glycyrrhiza glabra*) containing as acid β-glycyrrhetinic acid and its salts and/or its derivatives (glycyrrhetinic acid monoglucuronide, stearyl glycyrrhetinate, 3-stearoyloxyglycyrrhetic acid), ursolic acid and its salts, oleanolic acid and its salts, betulinic acid and its salts, extracts from plants such as *Paeonia suffruticosa* and/or *lactiflora, Laminaria saccharina, Boswellia serrata, Centipeda cunninghami, Helianthus annuus, Linum usitatissimum, Cola nitida, Epilobium angustifolium, Aloe vera, Bacopa monieri*, the salts of salicylic acid and in particular zinc salicylate, Canola oil, bisabolol and chamomile extracts, allantoin, Sepivital EPC (phosphoric diester of vitamin E and C) from Seppic, unsaturated omega-3 oils such as musk rose oil, blackcurrant oil, ecchium oil, or fish oil, plankton extracts, capryloyl glycine, Seppicalm VG (sodium palmitoylproline and nymphea alba) from Seppic, tocotrienols, piperonal, an extract of clove, phytosterols, cortisone, hydrocortisone, indomethacin and betamethasone.

The following may be particularly mentioned as examples of antimicrobials: 2,4,4'-trichloro-2'-hydroxydiphenyl ether (or triclosan), 3,4,4'-trichlorocarbanilide (or triclocarban), phenoxyethanol, phenoxypropanol, phenoxyisopropanol, hexamidine isethionate, metronidazole and its salts, miconazole and its salts, itraconazole, terconazole, econazole, ketoconazole, saperconazole, fluconazole, clotrimazole, butoconazole, oxiconazole, sulphaconazole, sulconazole, terbinafine, ciclopirox, ciclopiroxolamine, undecylenic acid and its salts, benzoyl peroxide, 3-hydroxybenzoic acid, 4-hydroxybenzoic acid, phytic acid, N-acetyl-L-cysteine acid, lipoic acid, azelaic acid and its salts, arachidonic acid, resorcinol, octopirox, octoxyglycerol, octanoylglycine, caprylyl glycol, 10-hydroxy-2-decanoic acid, dichlorophenyl imidazole dioxolan and its derivatives described in patent WO-A-93/18743, farnesol, phytosphingosines and their mixtures.

Examples of vitamins that can be used are the water-soluble or fat-soluble vitamins or provitamins such as vitamins A (retinol), C (ascorbic acid), B3 or PP (nicotinamide), B5 (panthenol), B6 or pyridoxine, E (tocopherol), K1, beta-carotene, and the derivatives of these vitamins and notably their esters, and mixtures thereof.

Additives

The composition of the invention can contain one or more additives, notably those that are anhydrous or in solid form (powder), selected from those generally employed in the cosmetic and dermatologic fields, for example sequestering agents, perfumes, antioxidants, preservatives, colouring matter (such as pigments and hydrophilic dyes) and mineral fillers and/or organic fillers, for example modified starch, such as that marketed under the designation Dry Flo by the company National Starch. If necessary, the additives can be encapsulated or adsorbed on powders.

Of course, a person skilled in the art will make sure that any of these additives and/or their amounts are selected in such a way that the advantageous properties that are intrinsic to the composition according to the invention will not, or substantially not, be adversely affected by the addition or additions envisaged.

In the field of skin care and/or cleansing, the article according to the invention can be used in various applications, notably for cleansing the skin and removal of make-up, treatment of the signs of ageing, treatment of greasy skin, hydration, photoprotection, and treatment of sensitive or sensitized skin to soothe it in the case of irritation. Thus, it can constitute for example a skin cleansing or make-up removal product, an exfoliator, a skin care product and notably a moisturizer, a rinsing patch, or a make-up product. It can also be used in the field of hair care, as a hair care product.

The article according to the invention can have different presentations depending on the intended use:

as a 2-in-1 applicator, the article being used for applying a product without being wetted and being wetted only after application of said product. For example, it can be used as an applicator of a substantially anhydrous make-up remover, the thermal effect being obtained by wetting the article after application of the make-up remover, or as an applicator of a mousse-forming toning product, by rehydrating the article in the hands;

as a single-dose product for rehydration, for example as warming exfoliating cream by moistening and dissolving the article in the hands;

as a rinsing patch, a patch being intended to be applied on a limited area: for example, as a freshening patch/gel for greasy skin, by moistening the area to be treated and applying the patch, which is transformed into a gel on the skin, and then removing it simply by rinsing;

as a 2-in-1 article: as a rinsing patch for the specific treatment of a limited area (application of the patch on the moistened area then rinsing after a waiting time) or as a single-dose product to be applied on a larger area, having moistened the product beforehand.

When the article is a cleansing or make-up removal product, a rinsing patch or a shampoo, it is typically necessary to rinse after application of the product and after a waiting time if applicable.

The examples below will serve to illustrate the invention, but without limiting its scope. The amounts stated are percentages by weight unless stated otherwise, and they correspond, unless stated otherwise, to the amount of raw material and not to the amount of active substance. The names of the compounds used are given as INCI name, as chemical name or as trade name.

EXAMPLES

The article used in the examples was made with a support of PVA-based Kuralon K-II WN2 fibres, which are soluble at a temperature less than or equal to 20° C. It was obtained by heat-sealing two layers, with a weight of 80 g/m$^2$, at their periphery. The article was in the form of a disc with a diameter of 3 cm, having a cavity in which the composition containing the compound with thermal effect was placed.

For Examples 1 and 3, the article contained 0.3 g of the compositions described.

For Examples 2 and 4, the article contained 0.5 g of the compositions described.

To use the article obtained in these examples, place it in the palm of the hand, wet it with about 2 to 4 ml of water and apply it on the face, or place it directly on the moistened skin. Then rinse the skin.

|  | Example 1 according to the invention: Mousse-forming toning product | Example 2 according to the invention: Exfoliating make-up removal cream |
| --- | --- | --- |
| Sodium cocoyl isethionate (1) | 40 | — |
| Potassium myristate | 40 | — |
| Urea | 20 | — |
| Modified starch (2) | — | 17.5 |
| $MgCl_2$ | — | 20 |
| Polyethylene powder (3) | — | 10 |
| Vaseline oil | — | 52.5 |

(1) Jordapon CIP (BASF)
(2) C* Flo 06205 (Cerestar)
(3) Microthene MN 727 (Equistar)

Example 1 was prepared by mixing the powders, then placing the mixture in the cavity of the support, which was then closed by heat-sealing.

Example 2 was prepared by making an O/W emulsion by mixing the compounds apart from $MgCl_2$ with about 70% of water, then removing the water by atomization and adding $MgCl_2$. The pulverulent mixture obtained was then placed in the cavity of the support, which was then closed by heat-sealing.

Example 1 contains urea, which gave a cold effect after hydration of the article, whereas Example 2 contains magnesium chloride, which gave a hot effect after hydration of the article.

|  | Example 3 according to the invention: Rinsing patch for greasy skin | Example 4 according to the invention: After-sun soothing patch |
| --- | --- | --- |
| Polyvinyl alcohol (1) | 40 | — |
| Carboxymethyl cellulose (2) | — | 70 |
| Salicylic acid | 10 | — |
| Zeolite (3) | 20 | — |
| Kaolin | 30 | — |
| Soothing active (4) | — | 2 |
| Urea | — | 28 |

(1) Celvol 540 PV alcohol (Celanese Chemical)
(2) Blanose 9M31F (Hercules)
(3) X-mol (Zeochem)
(4) N-acetyl-tyr-arg hexadecyl ester (Sederma)

Examples 3 and 4 were prepared by mixing the powders, then placing the mixture in the cavity of the support, which was then closed by heat-sealing.

Example 3 contains zeolite, which gave a hot effect after hydration, whereas Example 4 contains urea, which gave a cold effect after hydration.

The above written description of the invention provides a manner and process of making and using it such that any person skilled in this art is enabled to make and use the same, this enablement being provided in particular for the subject matter of the appended claims, which make up a part of the original description and including an article, in particular a cosmetic or dermatological article, comprising a support in the form of at least one sheet comprising fibres that are soluble in water at a temperature less than or equal to 30° C., said support having a density less than or equal to 0.1 g/cm³, and a composition carried by the support, containing at least one compound with thermal effect.

As used herein, the phrases "selected from the group consisting of," "chosen from," and the like include mixtures of the specified materials. Terms such as "contain(s)" and the like as used herein are open terms meaning 'including at least' unless otherwise specifically noted.

All references, patents, applications, tests, standards, documents, publications, brochures, texts, articles, etc. mentioned herein are incorporated herein by reference. Where a numerical limit or range is stated, the endpoints are included. Also, all values and subranges within a numerical limit or range are specifically included as if explicitly written out.

The above description is presented to enable a person skilled in the art to make and use the invention, and is provided in the context of a particular application and its requirements. Various modifications to the preferred embodiments will be readily apparent to those skilled in the art, and the generic principles defined herein may be applied to other embodiments and applications without departing from the spirit and scope of the invention. Thus, this invention is not intended to be limited to the embodiments shown, but is to be accorded the widest scope consistent with the principles and features disclosed herein.

The invention claimed is:

1. A cosmetic article, comprising:
   a support of at least one sheet comprising at least one fiber which is soluble in water at a temperature less than or equal to 30° C.; and
   a composition carried by the support;
   wherein
   a density of the support is less than or equal to 0.1 g/cm³, and
   the composition carried by the support comprises at least one compound which causes a temperature change due to an exothermic or endothermic reaction when contacted with water.

2. The article according to claim 1, wherein the at least one fiber that is water-soluble at a temperature less than or equal to 30° C. comprises polyvinyl alcohol.

3. The article according to claim 1, wherein the at least one sheet of the support is a nonwoven sheet.

4. The article according to claim 1, wherein the at least one sheet of the support further comprises a water-insoluble fiber.

5. The article according to claim 4, wherein an amount of the water-insoluble fiber is at most 40 wt. % relative to the total weight of the fibers of the at least one sheet of the support.

6. The article according to claim 1, wherein the support comprises at least two sheets, at least one of which comprises a fiber soluble in water at a temperature of 0-30° C.

7. The article according to claim 1, wherein
   the support comprises at least two sheets having a cavity between the at least two sheets, with at least one of the sheets comprising a fiber soluble in water at a temperature of 0-30° C.,
   and
   the cavity contains the composition comprising at least one compound which causes a temperature change due to an exothermic or endothermic reaction when contacted with water.

8. The article according to claim 7, wherein the at least two sheets having a cavity are nonwovens.

9. The article according to claim 8, wherein
   one of the at least two sheets is a nonwoven, consisting of fibers soluble in water at a temperature of 0-30° C., and the other of the at least two sheets is a nonwoven, consisting of water-insoluble fibers.

10. The article according to claim 7, wherein the at least two sheets are joined together at their periphery.

11. The article according to claim 10, wherein the sheets are joined together at their periphery by heat-sealing.

12. The article according to claim 1, wherein the support is completely soluble in water.

13. The article according to claim 1, wherein
an amount of the at least one compound which causes a temperature change due to an exothermic or endothermic reaction when contacted with water ranges from 10 to 100 wt. % relative to the total weight of the composition.

14. The article according to claim 1, wherein the at least one compound which causes a temperature change due to an exothermic or endothermic reaction when contacted with water is at least one exothermic compound selected from zeolites, exothermic inorganic salts, polyols having at least 2 hydroxyl groups and at least 3 carbon atoms, ethers of vanillyl alcohol, gingerol, capsaicin, eugenol, cinnamon oil, benzyl alcohol, and mixtures thereof.

15. The article according to claim 1, wherein the at least one compound which causes a temperature change due to an exothermic or endothermic reaction when contacted with water is at least one endothermic compound selected from endothermic inorganic salts, mint, urea, and mixtures thereof.

16. The article according to claim 1, wherein the at least one compound which causes a temperature change due to an exothermic or endothermic reaction when contacted with water or the composition containing the compound is a powder or paste.

17. The article according to claim 1, wherein an amount of the composition carried by the support is between 10 and 1000 wt. % relative to the weight of the support.

18. The article according to claim 1, wherein the composition carried by the support further comprises at least one compound selected from mousse-forming surfactants, water-soluble polymers, fats, oils, exfoliating agents, keratolytic agents, moisturizers, soothing agents, antimicrobials, and a mixture thereof.

19. The article according to claim 1, wherein the article is a skin cleansing or make-up removal product, an exfoliator, a skin care product, a rinsing patch, a hair care product, or a make-up product.

20. The article according to claim 1, wherein the support is one selected from the group consisting of a pad, a mask, a patch, a mobcap, a finger of a glove, a glove, a sheet for cutting out, a wipe, a disc, an oval and a rectangle.

* * * * *